US006923779B1

(12) United States Patent
Choiniere

(10) Patent No.: US 6,923,779 B1
(45) Date of Patent: Aug. 2, 2005

(54) BELT

(76) Inventor: Bruno Choiniere, 5507 Singer Ct., Granger, IN (US) 46530

( * ) Notice: Subject to any disclaimer, the term of this patent is extended or adjusted under 35 U.S.C. 154(b) by 55 days.

(21) Appl. No.: 10/890,921

(22) Filed: Jul. 14, 2004

(51) Int. Cl.[7] .............................................. A61F 13/00
(52) U.S. Cl. .......................................... 602/19; 2/311
(58) Field of Search .................. 602/19, 60; 128/96.1, 128/100, 876, 101.1, 100.1; 2/311, 312, 317, 2/318, 321, 324, 220, 310; D29/100, 101.3, D29/101.5

(56) References Cited

U.S. PATENT DOCUMENTS

| | | | |
|---|---|---|---|
| 4,721,102 A * | 1/1988 | Pethybridge ................. | 602/19 |
| 5,188,586 A * | 2/1993 | Castel et al. .................. | 602/19 |
| 5,267,947 A | 12/1993 | James et al. | |
| 5,407,422 A | 4/1995 | Matthijs et al. | |
| 5,569,171 A | 10/1996 | Muncy | |
| 5,737,774 A | 4/1998 | Petty-Saphon et al. | |
| 5,820,575 A * | 10/1998 | Cabrera et al. ................ | 602/19 |
| 5,833,638 A * | 11/1998 | Nelson ......................... | 602/19 |
| 6,419,652 B1 * | 7/2002 | Slautterback ................ | 602/19 |
| 6,676,617 B1 | 1/2004 | Miller | |
| 6,755,799 B2 * | 6/2004 | Toda ............................ | 602/19 |
| 2001/0027282 A1 * | 10/2001 | Baugh ........................... | 602/7 |
| 2003/0073942 A1 * | 4/2003 | Gibbs et al. .................. | 602/19 |

* cited by examiner

*Primary Examiner*—Kim M. Lewis
(74) *Attorney, Agent, or Firm*—Leo H McCormick, Jr.

(57) ABSTRACT

A process of manufacturing a belt wherein a plurality of strips of a first material are sewn together to create an outer member having a desired length with a plurality of vertical seams. A layer of a second material is placed over the seams and sewn thereto create a plurality of vertical slots. After staves are inserted in the slots, a layer of a resilient material is placed over the second material and a layer of perforated material is placed over the resilient material. A strip of material is placed on the peripheral surface of the inner and outer members and sewn to define the belt. First and second fasteners on the first and second side sections joined together to apply a force through the staves to provide support for an underlying area of the torso of an individual to assist in attaining a desired posture.

14 Claims, 5 Drawing Sheets

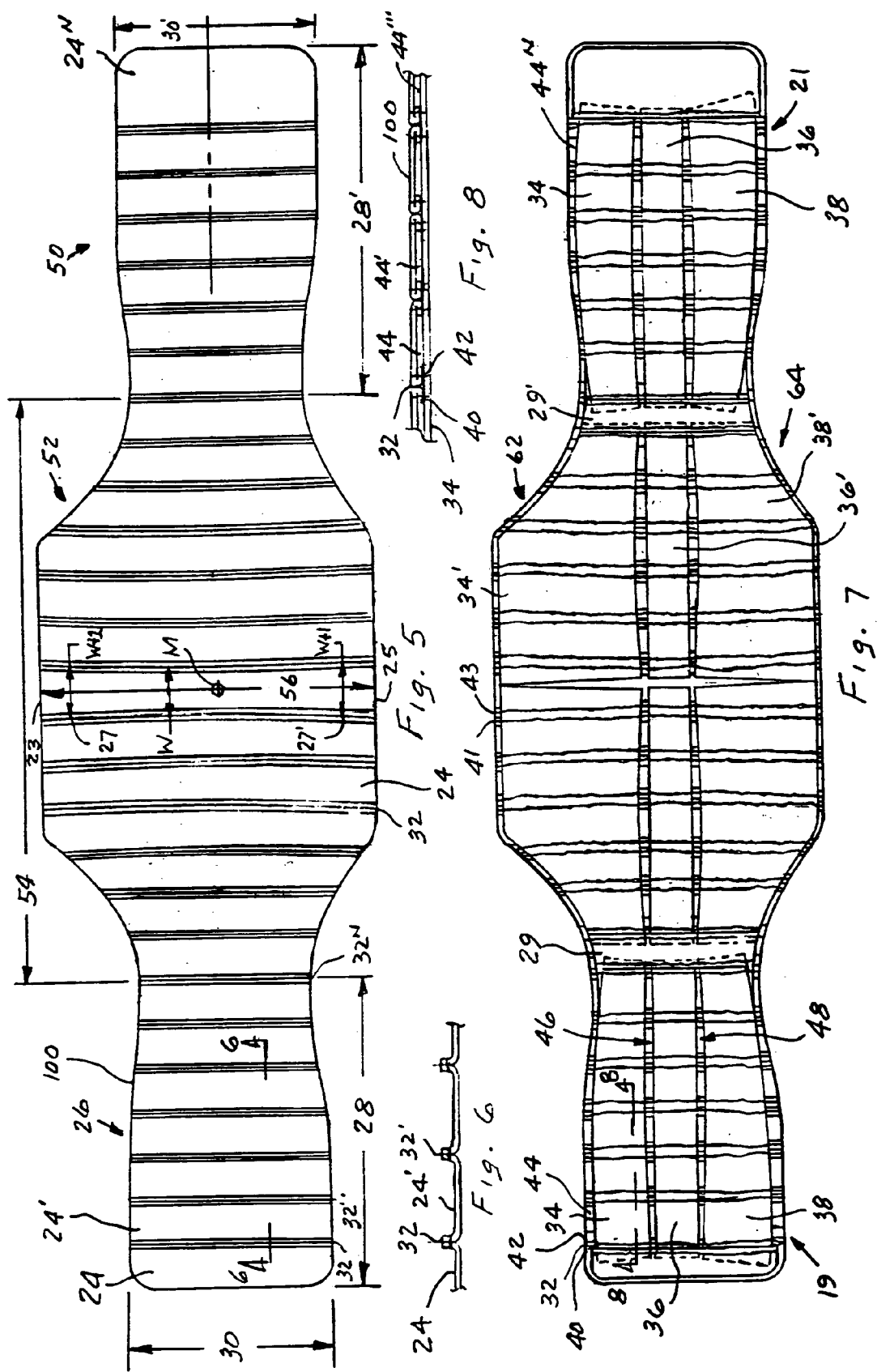

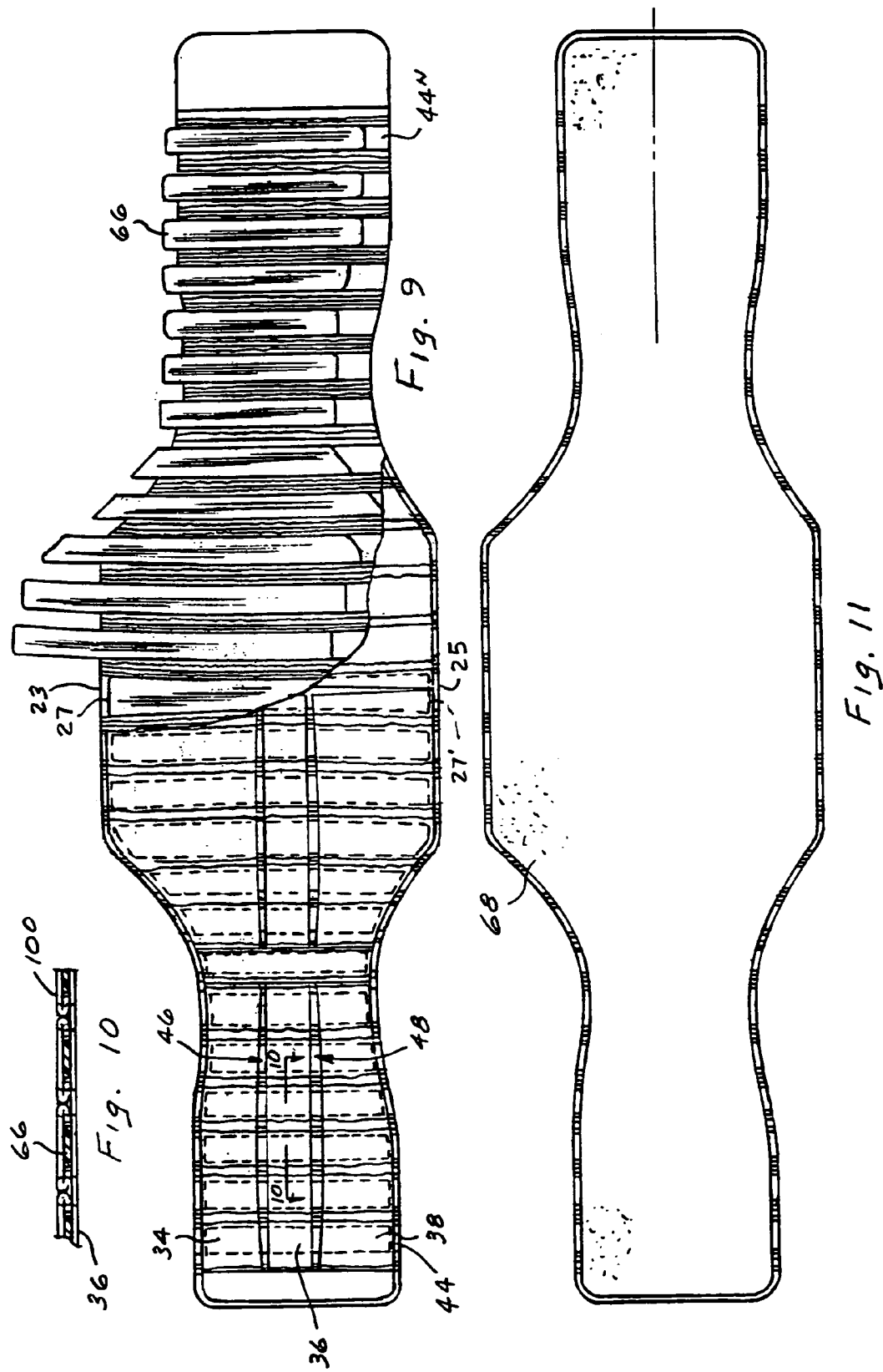

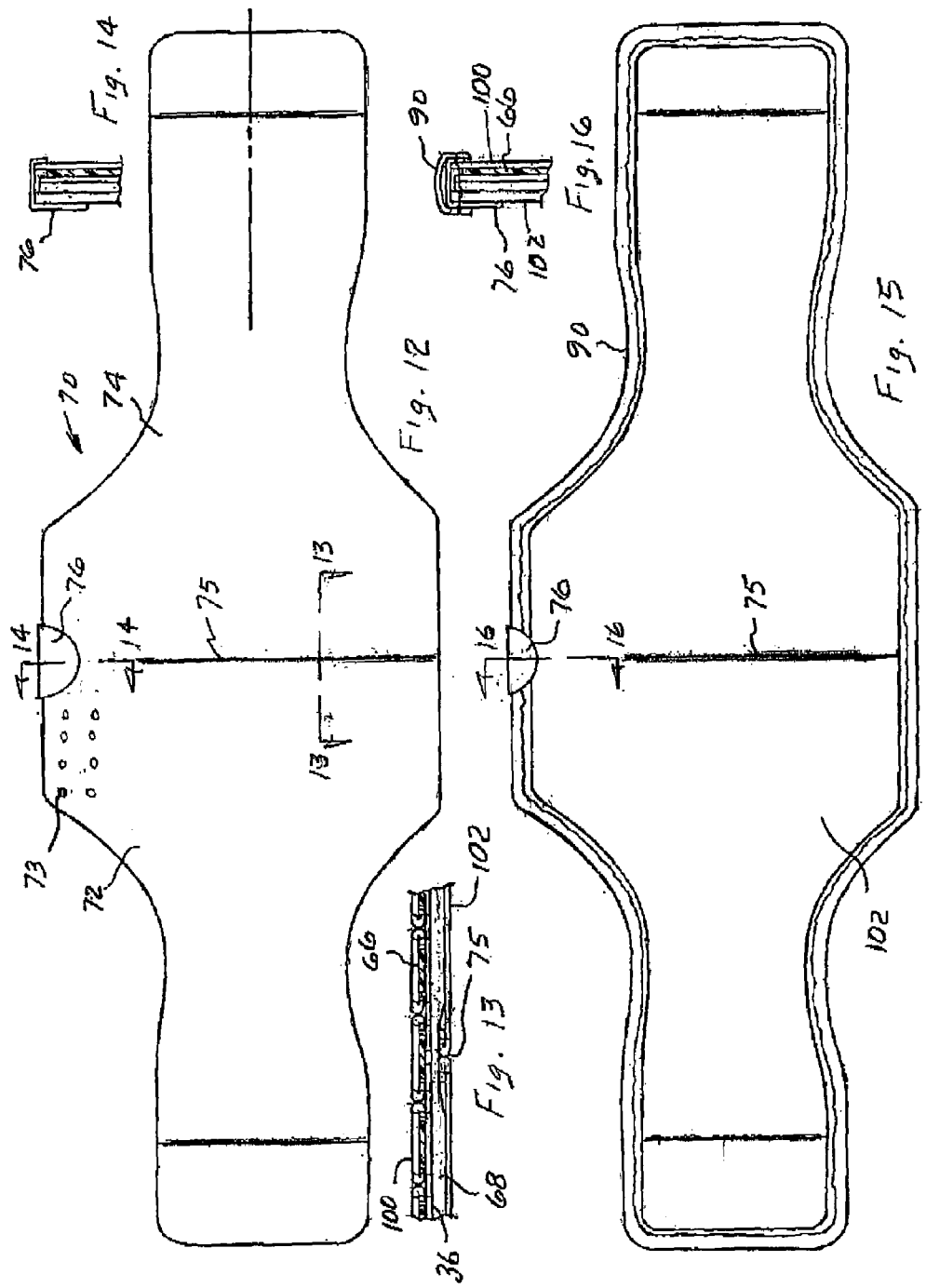

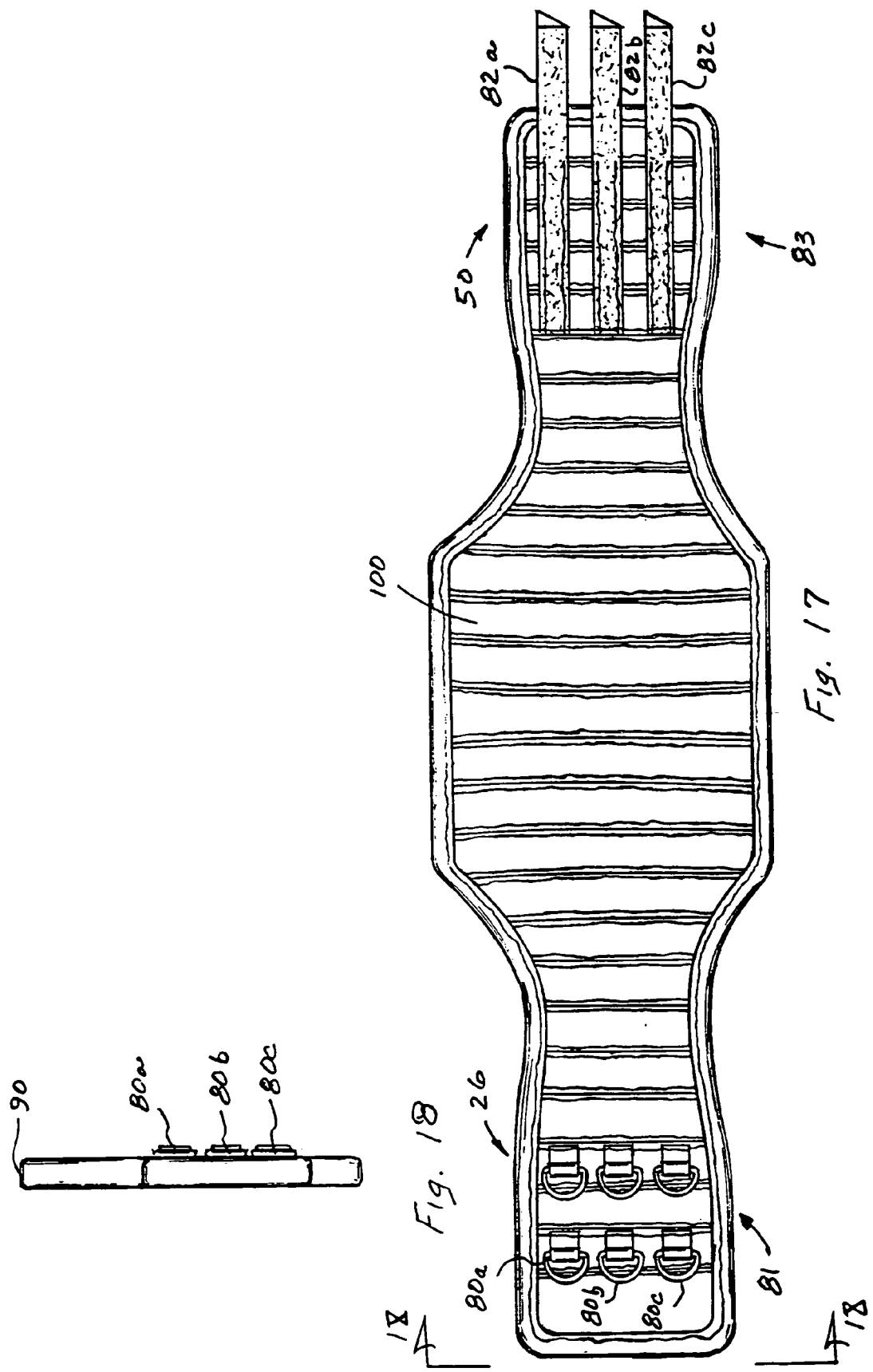

BELT

This invention relates to a belt for providing support to the torso of an individual having staves located in a plurality of vertical pockets that define a ring for gently applying pressure on an area underlying the belt to assist in attaining a desired pain free posture.

BACKGROUND OF THE INVENTION

Back pain is a common problem experienced by many people. Most low back pain is a result of soft tissue injure such as disc herniation of spinal disc that does not require surgery but may require the use of anti-inflammatory drugs and medication therapy. During rehabilitation it may be necessary for a person to employ some type of bracing, such as disclosed in U.S. Pat. Nos. 5,267,947; 5,407,422; 5,569,171; 5,737,774; and 6,676,617, to support the effect area and perform normal daily activities. The brace functions to alert the person of posture, flexion and movements that may expand the injury or extend the healing time for the person. However, if a brace is too rigid or continually worn by a person, the time for recovery of an injury to the soft tissue may be extended, as the person may become too dependent on the brace.

SUMMARY OF THE INVENTION

This invention provides a belt that provides support for soft tissue of the spine of a person such that a substantially constant force may be applied to vertebrae while a reduced force is applied as a pressure ring to the tissue surrounding the vertebrae to assist in achieving a desired posture.

In more particular detail, the belt is defined by inner and outer members with intermediate layers of a material there between to define a semi-rigid structure having a shape in center section that approximates the thoracio-lumbar vertebrae and sacro-coccygael of an individual. The outer member is created by sewing a plurality of strips of a first material together to create a desired length for the belt. The individual strips have a desired length such that on sewing the strips together, a plurality of vertical seams are created along an entire length of the belt and a center section is created that transitions into first and second side sections. The length of the center section and first and second side sections are about equal in defining the length of the belt. A first layer of an intermediate second material is placed over the outer member and attached thereto by sewing first and second parallel seams adjacent the plurality of vertical seams in the outer layer to create a corresponding plurality of vertical slots in the center and side sections. A stave is inserted in each slot and an intermediate layer of a third material is placed over the intermediate layer of the second material. The third material is an open pore sponge that has a resiliency such that it may be compressed on the application of a force. An inner member defined by a fourth material that has perforations therein to allow the communication of air there through is placed over the intermediate layer of third material. A binding defined by a strip of a fifth material is placed around the peripheral surface of the first, second, third and fourth materials and sewn to define a unitary structure wherein the plurality of staves are located in a vertical position along substantially the entire length of the resulting belt. A first fastener is attached to the first side section of the outer member and a second fastener member is attached to the second side section of the outer member. On positioning the belt on a torso of the individual, the first fastener and second fastener are joined together with a force to exert a corresponding constant force on the thoracio-lumbar vertebrae and sacro-coccygael and a variable force through the plurality of staves on the underlying area of the torso covered by the inner member such that a desired pain free posture may be attained.

An advantage of the present invention is achieved through a belt whereby a direct force may be applied to a specific area of the torso and a variable force applied to the area surrounding the specific area that allows flexible movement while providing support to soft tissue of the muscles associated with the movement.

A further advantage of this invention resides in a belt that is semi-rigid to provide support for soft tissue while allowing flexible movement for an individual to perform daily activities.

BRIEF DESCRIPTION OF THE DRAWINGS

FIGS. 5–18 illustrate a sequential process of manufacturing the belt illustrated in FIG. 3 and in particular;

FIG. 5 is a view an outer member of the belt;

FIG. 6 is a sectional view taken along lines 6—6 of FIG. 5;

FIG. 7 is a view of the outer member of FIG. 5 wherein a first intermediate member sewn to the outer member of FIG. 5 to define a plurality of vertical pockets;

FIG. 8 is a sectional view taken along lines 8—8 of FIG. 7;

FIG. 9 is a view of the outer member and first intermediate member a portion of which is removed to show staves that are inserted in the vertical pockets;

FIG. 10 is a sectional view taken along lines 10—10 of FIG. 9;

FIG. 11 is a view of a second intermediate member for the brace that is placed over the first intermediate member;

FIG. 12 is a view of an inner member for the brace that is placed over the second intermediate member;

FIG. 13 is a sectional view taken along lines 13—13 of FIG. 12;

FIG. 14 is a sectional view taken along lines 14—14 of FIG. 12;

FIG. 15 is a view of the assembly of FIG. 12 with binding attached about the peripheral surface;

FIG. 16 is a sectional view taken along lines 16—16 of FIG. 15;

FIG. 17 is a view of the belt with fasteners attached thereto; and

FIG. 18 is a view taken along lines 18—18 of FIG. 17.

DETAILED DESCRIPTION

In this application a same number may be used with respect to a different component if a same feature is present.

Figure 1:
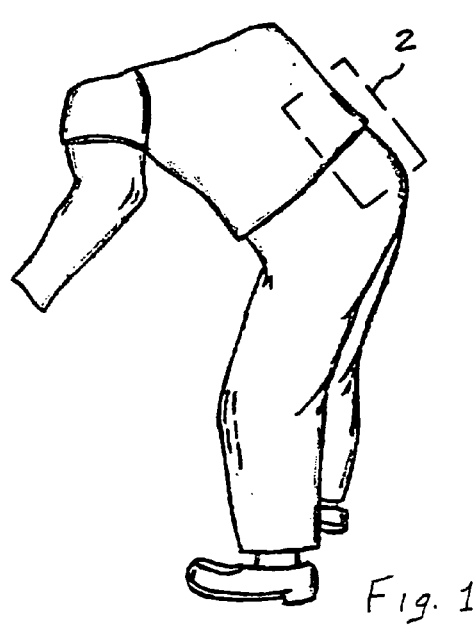
FIG. 1 is a perspective view of an individual illustrating a posture associated with a protruding disc of the spine of such an individual.
Figure 2:
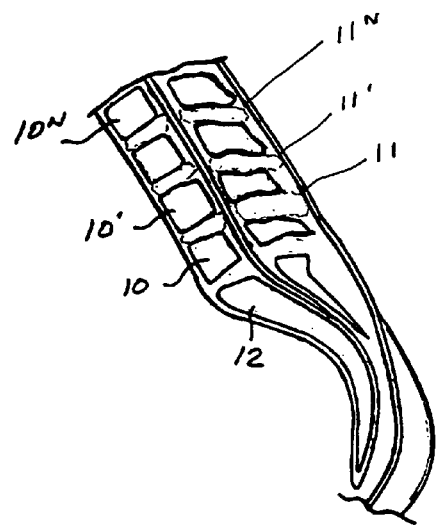
FIG. 2 is a sectional view of the spinal disc of the circumscribed area 2 of FIG. 1.
Figure 3:
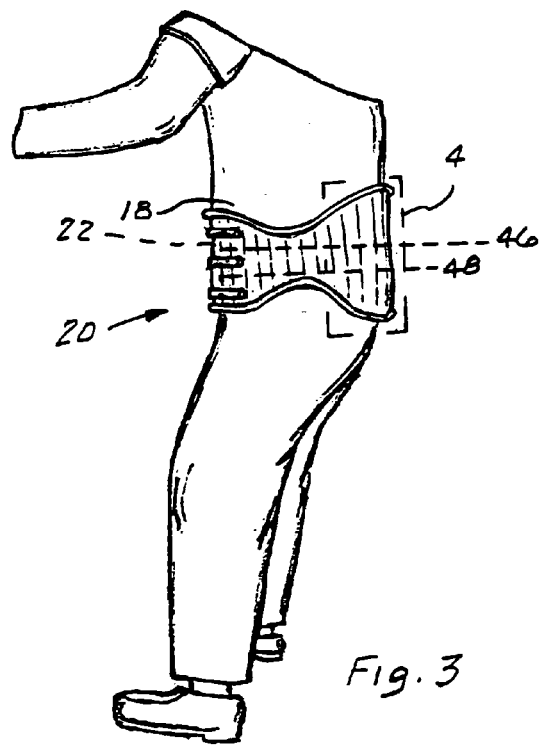
FIG. 3 is a perspective view of an individual having a belt, made according to the present invention, that is affixed to his lower torso to provide bracing and assist in achieving a desired posture.
Figure 4:
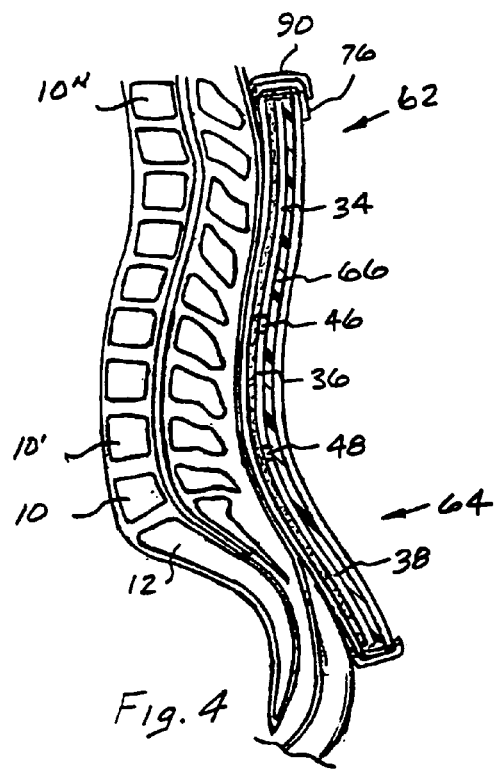
FIG. 4 is a sectional view of the spine of the circumscribed area 4 of the individual of FIG. 3.

An individual suffering from a strain or back injury may assume a posture, as illustrated in FIG. 1, as a result of pain associated therewith. In such a situation, one or more disc 11,11' ... 11" that separate the vertebrae of the thoracio-lumbar spine 10,10' ... 10", may extrude inwardly and bulging outwardly such that the curvature of the thoracio-lumbar spine 10,10' ... 10" may be changed and as a result act on nerves, as schematically illustrated in FIG. 2. Depending on the pain experiences by the individual, treatment for such injury may include rest, surgery, or strengthening exercises. In any event, in order for an individual to perform normal activities it may be advisable and/or necessary to wear a belt 20 around the lower region of torso 18, as illustrated in FIG. 3, to support the muscles and soft tissue in the area of the thoracio-lumbar vertebrae 10,10' ... 10". The belt 20 of the present invention is designed to provide a constant force or support for at least the second through the fourth lumbar vertebrae 10,10' ... 10", variable support up to the eighth/ninth thoracic vertebrae 10,10' ... 10" and cover the sacro-coccygael junction 12 to assist in achieving a desired posture that approximates a normal curvature of the spine as illustrated in FIG. 4. When the belt 20 firmly surrounds the torso 18 of an individual, hip and leg movement is not restricted provided and the stomach muscles 22 are also supported in a manner such the flow of blood to the muscles and soft tissue is not restricted and as a result the time to heal the injured tissue may be reduced. The belt 20 provides a constant force to the center section of the belt and a variable force that is gentle to provides a massage effect to the soft tissue underlying the belt to ease any discomfort and pain the individual may experience.

In more particular detail, the belt 20 is defined by a plurality of layers of material that form a semi-rigid structure and may be manufactured through the following process.

A first plurality of strips 24,24' ... 24" of a first material are sewed together see FIG. 5, to create a first side section 26 for an outer member 100 having a first length 28 and a first width 30 to define a shape with a plurality of vertical seams 32,32' ... 32", as illustrated in FIG. 6. The preferred first material is leather having a thickness of about 3 ply.

First 34, second 36 and third 38 pieces of a intermediate second material are layered over the first side section 26, see FIG. 7, and sewed along the plurality of vertical seams 32, 32' ... 32" to create vertical seams 40 and 42 adjacent each vertical seam and thereby produce a plurality of vertical slots 44, 44' ... 44" in the first side section 26, as illustrated in FIG. 8. The space between the edges of the first 34, second 36 and third 38 pieces of the second material define linear hinges 46 and 48 such that the area covered by the upper first piece 34 and the area covered by the lower third piece 38 may independently flex with respect to the second piece 36. The preferred second material is suede leather.

A second plurality of strips 24,24' ... 24" of the first material are sewn together to create a second side section 50 having a same first length 28' and a same first width 30' to define a shape for a second side section 50 with a plurality of vertical seams 32,32' ... 32", as the first side section 26 illustrated in FIG. 5.

As with the first side section 26, first 34, second 36 and third 38 pieces of the intermediate second material for the second side section 50 are layered over the second side section 50 and sewed along the plurality of vertical seams 32, 32' ... 32" to create first and second vertical seams 40 and 42 to produce a plurality of vertical slots 44, 44' ... 44" in the second side section 50. The space between the edges of the first 34, second 36 and third 38 pieces of the second material for the second side section 50 also define linear hinges 46 and 48 such that the area covered by the first piece 34 and the area covered by the third piece 38 may independently flex with respect to the second piece 36. The first 26 and second 50 side sections are complementary and designed such that the length of a section may be changed by adding additional strips 24 of the first material at a transition point 29, 29'.

A third plurality of strips 24,24' ... 24" of a first material are sewn together to create a center section 52 having second length 54 and a second width 56 with a plurality of vertical seams 32,32' ... 32", to define a shape as illustrated in FIG. 5.

First 34', second 36' and third 38' pieces of the intermediate second material are layered over the center side section 52 and sewed adjacent the plurality of vertical seams 32, 32' ... 32" to create first and second vertical seams 41 and 43 and ultimately the plurality of vertical slots 44,44' ... 44" in the center section 52 that are parallel to the vertical slots in the first 26 and second 50 side sections.

A strip 24 of the first material for at least the center section 52 is defined by a desired length having a first end 23 and a second end 25 with a first width "W" at a mid-point "m" between the first end 23 and the second end 25 that expands to a second width "W+1" at a points 27, 27' respectively located adjacent the first 23 and second 25 ends. When the plurality of strips 24 are sewed together to define a length 54 for the center section 52, a desired vertical arc is created between the first end 23 and the second end 25 that is designed to approximate the shape of the thoracio-lumbar vertebrae 10,10' ... 10" of the spine of an individual as illustrated in FIG. 4.

The first side section 26 is sewn to the center section 52 at a transition point 29 and the second side section 50 is sewn to the center section 52 at a transition point 29' to define a desired length for a resulting belt 20, as shown in FIG. 5. With the first side section 26 and second side section 50 sewn to the center section 52 a central section having a uniform width defined by the second piece 36 of the second intermediate material substantially extends along the entire length of the belt 20, while an upper section 62 has a first variable width that substantially extends along the entire length of the belt 20 and a lower section 64 has a second variable width that substantially extends along the entire length of the belt 20.

The plurality of vertical slots 44,44' ... 44" substantially extend from the first end 19 to the second end 21 and each receive a corresponding stave 66 as illustrated in FIGS. 9 and 10. The staves on being inserted in the slots 44, 44' ... 44" are designed to extend to approximately the points 27, 27' adjacent the first 23 and second 25 ends of the strips 24 of the first material.

Once a stave 66 is placed in each slot 44,44' ... 44", a single piece 68 of an intermediate third material that has a uniform thickness, see FIG. 11, is placed over the entire length and width of the outer member 100 with the layer of the first 34', second 36' and third 38' pieces of the intermediate second material attached thereto. The intermediate third material is preferred to be a sponge material that has a resiliency that is compressible on the application of a force thereto.

Next, a layer 70 having a first member 72 and a second member 74 of a fourth material is placed over the layer of the single piece 68 of the third material to define an inner member 102 for the belt 20, see FIGS. 12 and 13. The first member 72 and second member 74 are complimentary and have a seam 75 that is located at the mid-section of the center section 52 of the outer member 100. The fourth material is preferred to be leather that has perforations 73,73' ... 73" therein, only a few of which are shown, allow the communication of air there through.

Thereafter, a centering tab 76 is placed located at the top of the seam 75, see FIG. 14 and a binding strip 90 of a fifth material placed to cover the peripheral surfaces of the first, second, third and fourth materials, see FIGS. 15, and 16. The binding strip 90 is sewn to secure the inner member 102 to the outer member 100 such the stave 66 in the slots 44, 44' ... 44" are retained in a vertical position with respect to the length of the belt 20.

A first fastener arrangement 81 consisting of loop members 80a,80b and 80c are attached to the first side section 26 and a second fastener arrangement 83 consisting of straps 82a, 82b and 82c are attached to the second side section 50, see FIGS. 17 and 18. Loop member 80b and strap 82b are aligned located along the center line of the length of the belt 20 while loop member 80a and strap 82a and loop member 80c and strap 82c are located in an alignment above the hinges 46 and 48.

When the first 81 and second 83 fastener arrangements are attached to the first 26 and second 50 side sections, the manufacture of belt 20 is completed.

The plurality of strips 24,24' ... 24" that make up the outer member 100 may be sewn together and the first 34, second 36 and third 38 pieces sequentially attached thereto to define the plurality of vertical slots 44,44' ... 44" when a quantity of belts have a same or fixed length rather that making the first 26 and second 50 side sections and then attaching them to the center section 52.

Method of Use

Belt 20 is placed on the lower torso 18 of an individual and with the centering tab 76 located along the vertical axis of the spine such that the upper section 62 reaches to approximately the ninth thoracic vertebrae, the center section 52 covers the second through the fourth lumbar vertebrae and the lower section 64 covers sacro-coccygael 12. With belt 20 firmly secured to the individual, a force applied through the center section 52 is constantly applied to the second through the fourth lumbar vertebrae while a variable force is applied to the soft tissue adjacent the center section 52 through the staves 66 act to assist in achieving a desired posture that approximates a normal curvature of the spine as illustrated in FIG. 4. The side sections 26 and 50 are designed to hold to intestines at the front of the waist of the individual upward toward the chest. Because of water retention by the intestines, the organs in the abdomen have a tendency to drop resulting in stretching of blood vessels associated with the organs and as a result the effectively efficiency of the organs may be reduced. By supporting the abdomen, the blood vessels return to a normal size and allow unrestricted circulation of blood through to organs and contribute to the return of normal functioning including the healing of injured tissue associated with the thoracio-lumbar vertebrae.

I claim:

1. A process of manufacturing a belt that is designed to be located on the torso of an individual to assist in attaining a desired posture, including the steps of:

sewing a plurality of strips of a first material together to create a plurality of vertical seams and define a center section that transitions into first and second side sections having a desired length wherein the length of each of said center section and first and second side sections are about equal to define an outer member for said belt;

placing a layer of an intermediate second material over said outer member and sewing along said plurality of vertical seams to define a corresponding plurality of vertical slots in said center and side sections;

inserting staves in said slots;

placing a first layer of an intermediate third material over said intermediate second material, said layer of intermediate third material having a resiliency that is compressible on the application of a force thereto;

placing a fourth material over said layer of intermediate third material to define an inner member for said belt, said fourth material having perforations therein to allow the communication of air there through;

covering the peripheral surface of said first, second, third and fourth materials with a strip of a fifth material to define a binding cuff;

sewing the fifth material to secure the inner member to the outer member such that the plurality of staves are retained in a vertical position with respect to the length of the belt;

attaching a first fastener to said first side section of said outer member; and attaching a second fastener member to said second side section of said outer member such that on positioning said belt on a torso of the individual and joining said first fastener with said second fastener a force may be applied through said plurality of staves to support an underlying area of the torso adjacent the inner member.

2. The process of manufacturing a belt as recited in claim 1 wherein said first layer of intermediate first material is defined by a center section having a first width that substantially extends along the entire length of the belt, an upper section having a first variable width that substantially extends along the entire length of the belt and a lower section having a second variable width that substantially extends along the entire length of the belt, and wherein said sewing of said intermediate layer first along said plurality of vertical seams to create said corresponding plurality of vertical slots produces first and second linear hinges adjacent said center section such that the force applied to secure said first fastener with the second fastener is applied to the underlying area as a sum of a direct force through the center section and variable forces through the upper and lower sections.

3. The process of manufacturing a belt as recited in claim 2 wherein each strip of said first material in said center section is defined by a length having a first end and a second end with a first width at a mid-point between said first end and said second end that expands to a second width at a point adjacent the first and second ends, said sewing of said strips together to define a length for said center section creating a desired vertical arc to be created between said first end and said second end that is designed to approximate the shape of the thoracio-lumbar spine of an individual.

4. The process of manufacturing a belt as recited in claim 3 wherein the width of said center section is designed to engage at least the second through the fourth lumbar vertebrae, the lower section reaches to the sacro-coccygael and upper section reaches up to the eighth and ninth thoracic vertebrae to provide support for achieving the desired posture.

5. The process of manufacturing a belt as recited in claim 4 wherein the length of said center section may be changed by adding an equal number of strips said first material about a center strip located at a mid-point of said length of said center section.

6. The process of manufacturing a belt as recites in claim 5 wherein the length of said side section may be changed by adding an equal number of strips of said first material at the transitions points between with the first and second sections and said center section.

7. The process of manufacturing a belt as recited in claim 6 further including the placing of a tab on the inner member to define a center of said center section.

8. The belt defined by the process in claim 7.

9. A process of manufacturing a belt that is designed to be located on the torso of an individual to assist in attaining a desired posture, including the steps of:

sewing a first plurality of strips of a first material together to create a first side section having a first length and a first width, said first side section having a plurality of vertical seams;

placing a layer of an intermediate second material over said first side section and sewing along said plurality of vertical seams to define a corresponding plurality of vertical slots in said first side section;

sewing a second plurality of strips of said first material together to create a second side section having said first length and said first width, said second side section having a plurality of vertical seams;

placing a layer of said intermediate second material over said second side section and sewing along said plurality of vertical seams to define a corresponding plurality of vertical slots in said second side section;

sewing a third plurality of strips of a first material together to create a center section having second length and a second width, said center section having a plurality of vertical seams;

placing a layer of said intermediate second material over said center section and sewing along said plurality of vertical seams to define a corresponding plurality of vertical slots in said center section;

connecting said first side section and said second side section to said center section to define an outer member for said belt having a desired length wherein the length of said first and second side sections is about equal to said second length of said center section;

placing a layer of an intermediate second material over said outer member and sewing along said plurality of vertical seams to define a corresponding plurality of vertical slots in said center and side sections;

inserting staves in said slots;

placing a first layer of an intermediate third material over said intermediate second material, said layer of intermediate third material having a resiliency that is compressible on the application of a force thereto;

placing a fourth material over said layer of intermediate third material to define an inner member for said belt, said fourth material having perforations therein to allow the communication of air there through;

covering the peripheral surface of said first, second, third and fourth materials with a strip of material to define a binding;

sewing the fifth material to secure the inner member to the outer member such that the plurality of staves are located in a vertical position with respect to the length of the belt;

attaching a first fastener to said first side section of said outer member; and attaching a second fastener member to said second side section of said outer member such that on positioning said belt on a torso of the individual and joining said first fastener with said second fastener a force may be applied through said plurality of staves to support an underlying area of the torso adjacent the inner member.

10. The process of manufacturing a belt as recited in claim 9 wherein said first layer of intermediate first material is defined by a center section having a first width that substantially extends along the entire length of the belt, an upper section having a first variable width that substantially extends along the entire length of the belt and a lower section having a second variable width that substantially extends along the entire length of the belt, and wherein said sewing of said intermediate layer first along said plurality of vertical seams to create said corresponding plurality of vertical slots produces first and second linear hinges adjacent said center section such that the force applied to secure said first fastener with the second fastener is applied to the underlying area as a sum of a direct force through the center section and variable forces through the upper and lower sections.

11. The process of manufacturing a belt as recited in claim 10 wherein each strip of said first material in said center section is defined by a length having a first end and a second end with a first width at a mid-point between said first end and said second end that expands to a second width at a point adjacent the first and second ends, said sewing of said strips together to define a length for said center section creating a desired vertical arc to be created between said first end and said second end that is designed to approximate the lumbar shape of the spine of an individual.

12. The process of manufacturing a belt as recited in claim 11 wherein the width of said center section is designed to engage at least the second through the fourth lumbar vertebrae, the lower section covers to the sacro-coccygael and upper section reaches up to the eighth and ninth thoracic vertebrae to provide support for achieving the desired posture.

13. The process of manufacturing a belt as recited in claim 12 wherein the length of said center section may be changed by adding an equal number of strips said first material about a center strip located at a mid-point of said length of said center section.

14. The process of manufacturing a belt as recites in claim 13 wherein the length of said side section may be changed by adding an equal number of strips of said first material at the transitions points between with the first and second sections and said center section.

* * * * *